United States Patent [19]
Fujinami et al.

[11] 3,939,838
[45] Feb. 24, 1976

[54] ARTICLE FOR TREATING MENSTRUAL FLUID

[75] Inventors: Nobuakira Fujinami, Yokosuga; Tadashi Nagano, Tokyo, both of Japan

[73] Assignee: Unicharm Kabushiki Kaisha, Kawanoe, Japan

[22] Filed: Aug. 20, 1974

[21] Appl. No.: 498,893

[52] U.S. Cl. .......... 128/290 R
[51] Int. Cl.² .......... A61F 13/16
[58] Field of Search .... 128/284, 287, 290 R, 290 P, 128/296, 285

[56] References Cited
UNITED STATES PATENTS

| | | | |
|---|---|---|---|
| 2,418,907 | 4/1947 | Schreiber | 128/290 R |
| 2,634,229 | 4/1953 | de Wet | 128/284 X |
| 3,340,875 | 9/1967 | Dudley et al. | 128/290 R |
| 3,490,454 | 1/1970 | Goldfarb | 128/290 R |
| 3,691,271 | 9/1972 | Charle | 128/290 R X |
| 3,762,415 | 10/1973 | Morrison | 128/290 R |
| 3,794,034 | 2/1974 | Jones, Sr. | 128/290 R |
| 3,804,094 | 4/1974 | Manoussos | 128/290 R |
| 3,856,014 | 12/1974 | Yamauchi | 128/290 R |

*Primary Examiner*—Aldrich F. Medbery
*Attorney, Agent, or Firm*—Fred Philpitt

[57] ABSTRACT

An article for treating menstrual fluid employs a cover member forming an enclosure, an absorbent layer positioned within the enclosure for absorbing the menstrual fluid, a water-proofing layer also positioned within the enclosure for preventing the menstrual fluid absorbed by the absorbent layer from permeating to the outside of the cover member and a deodorizer composition such as active carbon and the like located within the enclosure and having the function of absorbing and holding the menstrual fluid and simultaneously removing the odor released from the menstrual fluid.

2 Claims, 7 Drawing Figures

ARTICLE FOR TREATING MENSTRUAL FLUID

BACKGROUND OF THE INVENTION

This invention relates to an article, such as a sanitary napkin, sanitary pad and the like, having a deodorizer composition for absorbing and holding the menstrual fluid and simultaneously removing the odor released from the menstrual fluid.

The articles for treating menstrual fluid of the prior art have certain disadvantages. For instance, conventional articles for treating menstrual fluid have merely had the function of only absorbing and holding the menstrual fluid and exudates discharged from the body, and have heretofore paid no consideration to the so-called menstrual odor that is released from the menstrual fluid and exudates. Therefore, this has been an inconvenience to the women during their monthly periods and the persons who happened to be in contact with such women feel uncomfortable, and such persons come to know that such women are in their monthly periods of illness.

The present invention is intended to obviate the above mentioned difficulties, and especially to avoid the occurrence of the odor effect from the moment of application of the deodorant composition.

SUMMARY OF THE INVENTION

The present invention relates generally to an article for treating menstrual fluid and, more particularly, to sanitary napkins, sanitary pads, and the like for absorbing and holding the menstrual fluid and simultaneously removing the odor released from the menstrual fluid and exudates.

It is accordingly a primary object of the invention to provide an article for treating menstrual fluid having the function of effectively removing the odor that is released from the menstrual fluid, in addition to the function of absorbing and holding the menstrual fluid, and further being capable of solving said conventional inconvenience because the deodorizing capacity is extremely large as compared with the conventional articles of the same kinds.

Another object of the present invention is to provide a multilayer sanitary napkin having a high capacity for retaining the menstrual fluid and simultaneously removing the odor released from the menstrual fluids and exudates.

With the above and other objects in view, the present invention is characterized in that a deodorizer composition is interposed in a proper portion in the article for treating menstrual fluid which comprises an absorbent layer that absorbs the menstrual fluid, a water-proofing layer that prevents the menstrual fluid absorbed by the absorbent layer from permeating to the outside, and a cover member that wholly covers both said layers.

DETAILED DESCRIPTION OF THE INVENTION

Figure 1:
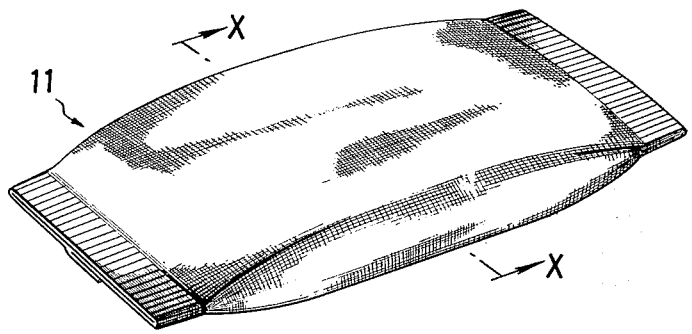
FIG. 1 is a perspective view showing the outward appearance of each of the embodiments of the sanitary napkins of the present invention.

Referring now to the drawings, a sanitary napkin 11 in FIG. 1 shows the outward appearance of a sanitary napkin according to each of the embodiments shown in FIGS. 2 to 6. In napkins 21, 31, 41, 51 and 61 shown in FIGS. 2 to 6 respectively, the following inner piled members are respectively covered with cover members 22, 32, 42, 52 and 62 so that the longitudinal portions of each cover member are properly superposed in the bottom face of each napkin, and simultaneously the width portions material each cover member are sealed. As to the materials of the cover members, a porous non-woven sheet prepared by mixing cellulose fiber with an artificial fiber is used so as to have a proper wet strength. Moreover, when a proper amount of a thermofusible fiber is mixed with the non-woven fiber, there occurs an advantage that the width portions are easily sealed by thermal adhesion under pressure, and also the cellulose fiber is treated for water-resisting, if necessary.

The napkins 21, 31, 41, 51 and 61 of the embodiments shown respectively in FIGS. 2, 3, 4, 5 and 6 include respectively absorbent layers 23, 33, 43, 53 and 63 for absorbing the menstrual fluid and water-proofing layers 24, 34, 44, 54 and 64 for preventing the menstrual fluid absorbed by each absorbent layer from permeating from the undersurface of each napkin. Each of the water-proofing layers is positioned under the respective absorbent layer. Each of the respective napkins also include water-proofing layers 25, 35, 45, 55 and 65 for preventing the menstrual fluid absorbed by each absorbent layer from permeating from the longitudinal portions of each napkin. Each of the water-proofing layers 25, 35, 45, 55 and 65 is positioned so as to cover the undersurface and the longitudinal side portions of each absorbent layer. Web, piled body of thin sheets, powdery material, and the like made of cellulose fiber are used for the absorbent layers 23, 33, 43, 53 and 63. A sheet made of cellulose fiber forming a thin film made of a resin, for instance, polyethylene, polypropylene, PVA, and the like is used for the water-proofing layers 24, 34, 44, 54 and 64. A paper prepared from cellulose fiber to which a water-proofing agent, for instance, a wax sizing agent, a petroleum resin sizing agent, or the like is added is used for the water-proofing layers 25, 35, 45, 55 and 65.

Figure 5:
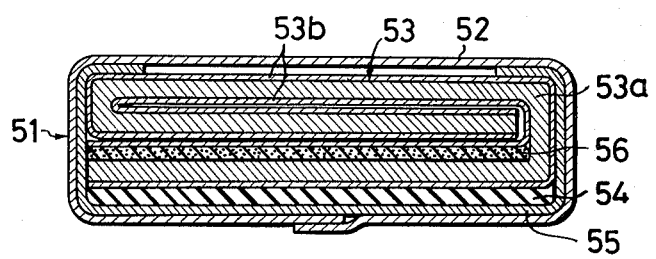
FIGS. 5 and 6 are sectional views taken along the X—X line in the FIG. 1 showing slightly modified forms of the napkin embodiments shown in FIGS. 2 and 4.
Figure 6:
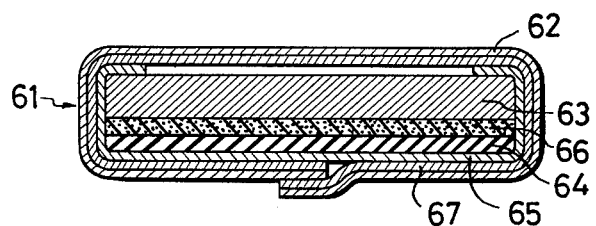

Napkins 51 and 61 of embodiments shown respectively in the FIGS. 5 and 6 are slightly modified forms of the structure of the napkins 21, 31 and 41. Namely, the absorbent layer 53 of the napkin 51 shown in FIG. 5, is spirally folded with covering web 53a with elasticity in the direction of thickness by a thin sheet 53b. A cottony thin web 67 having a low fiber density such as defatted cotton, rayon staple cotton, sodium CMC cotton, or the like is attached to the inside of the cover member 62 of the napkin 61 shown in the FIG. 6. Therefore, there occurs an advantage that the napkin 61 makes the contact with an user further comfortable, and the air permeability in the napkin area becomes preferable because of the porosity between the cover member 62 and the absorbent layer 63. Simultaneously the napkin has a function of spot-like absorption whereby the menstrual fluid that is discharged to the upper surface of the cover member 62 immediately attains to be absorbed by the absorbent layer 63 without widely staining the upper surface by widely permeating and dispersing within the enclosure of the cover member. Consequently, the napkin has an advantage that the user does not feel uncomfortable, and even in case the following deodorizer is separated from the holding fiber of the absorbent layer for some reason, the deodorizer is enclosed in the second water proof layer 65, thereby preventing the outside of the napkin from staining, or preventing the deodorizer from being exposed from the outside.

Most important characteristic of the present invention is to interpose a material for deodorizing the menstrual fluid in the napkin. Active carbon, active silica, active alumina, ion exchange resin, chlorophyl, and the like are used as the deodorizers. The deodorizer is interposed between the absorbent layer and the water-proofing layer, or in the absorbent layer and/or the water-proofing layer. Namely, the deodorizer is contained in sheets 26, 56 and 66 that are made of cellulose fiber interposed between the respective absorbent layers 23, 63 and the respective water-proofing layers 24, 64 in the sanitary napkins 21 and 61 shown in the FIGS. 2 and 6. Further, the deodorizer is respectively contained: in the absorbent layer 33 in the sanitary napkin shown in the FIG. 3; in the water-proofing layer 44 in the sanitary napkin 41 shown in the FIG. 4, and in a sheet 56 made of cellulose fiber interposed between the absorbent layer 53 and the waterproofing layer 54 in the sanitary napkin 51 shown in the FIG. 5.

There are many methods of making the deodorizer contents in each napkin. For instance, a method in which 80 to 240 mesh powder of active carbon, active silica, active alumina, and ion exchange resin is mixed with cellulose fiber to prepare a paper, or a method in which the powdery deodorizer is dispersed into a cottony web, piled body of thin paper, or powdery material made of cellulose fiber. The former example is shown respectively in the napkins 21, 41, 51 and 61 in FIGS. 2, 4, 5 and 6 as the layers 26, 44, 56 and 66, and the latter example is shown in the napkin 31 in FIG. 3 as the layer 33. Then the addition amount of active carbon, active silica, active alumina, and ion exchange resin is regulated so that, for instance, one napkin of 6 g contains 1 to 8% by weight of the deodorizer. Also, chlorophyl, for instance, dissolved in an organic solvent to regulate the concentration to 20 to 40% is preferably adhered to an absorbent sheet made of cellulose fiber by spraying, and the addition amount of the chlorophyl crystal is regulated so that one napkin of 6 g contains 1 to 8% by weight of the chlorophyl crystal, interposed in the layers 26, 56 and 66 in the napkins 21, 51 and 61 shown respectively in FIGS. 2, 5 and 6.

Figure 4:
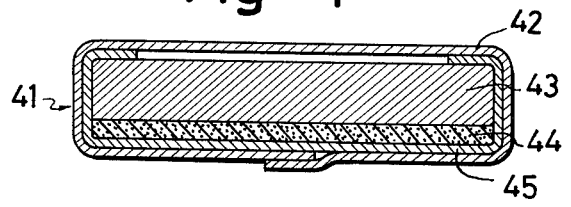
FIG. 4 is a sectional view taken along the X—X line in the FIG. 1 showing yet another embodiment.

Attention is directed to a case where the powdery deodorizer such as active carbon, and the like is contained in water-proofing layer 44 of the napkin 41 shown in the FIG. 4. For instance, the resin for applying the water-proofing function to the water-proofing layer is positioned to the undersurface of the water-proofing layer 44 in the FIG. 4 so that the absorptive surface of the deodorizer is not covered with the film resin.

In each napkin formed as described above, the odor of the menstrual fluid can be removed by the deodorizer interposed therein. As further described in detail, in a case where active carbon, active silica, active alumina, and ion exchange resin are interposed in the inside of the napkin, the odor from the menstrual fluid is absorbed by very small holes of the surface of the deodorizer. In a case where chlorophyl crystal is interposed in the inside of the napkin, the odor from the menstrual fluid is cancelled or weakened by the chlorophyl. Consequently, users of such napkins do not feel uncomfortable by the odor.

Also, active carbon can be said to be most suitable as a deodorizer in the present invention, since the active carbon has an extremely developed fine porous structure because of being a fine crystalline carbon. Thus it has an excellent absorption for low concentration gas, water-insoluble gas and many component system gas, and has a selective performance that though a material having large polarity such as water is not so absorbed, a material having small polarity is absorbed, and even if water is absorbed, water is extruded in contact with the odor gas, or the other gases having small polarity to absorb those gases, and so on.

In order to more fully understand the invention, the following examples are set forth:

Example 1

The structure of the sanitary napkin was formed similarly to the sanitary napkin in FIG. 5 described above. A non-woven sheet which was made with a wet-type paper preparation method by mixing cottony pulp to rayon staple cotton was used for the cover member 52. A cottony pulp web was used for the absorbent layer 53a. An absorbent tissue paper was used for the absorbent layer 53b. A paper was prepared from a mixture of pulp and carboxymethyl cellulose, subsequently forming a thin film of polyethylene thereon was used for the water-proofing layer 54. A paper was prepared from pulp to which a wax sizing agent was added was used for the water-proofing layer 55. A pulp sheet containing 30% by weight of 120 mesh active carbon powder per 25 g/m$^2$ of the scaled amount was used as the deodorizing member 56. Then the ratio of active carbon was 3% by weight for one sanitary napkin of 6 g.

Figure 7:
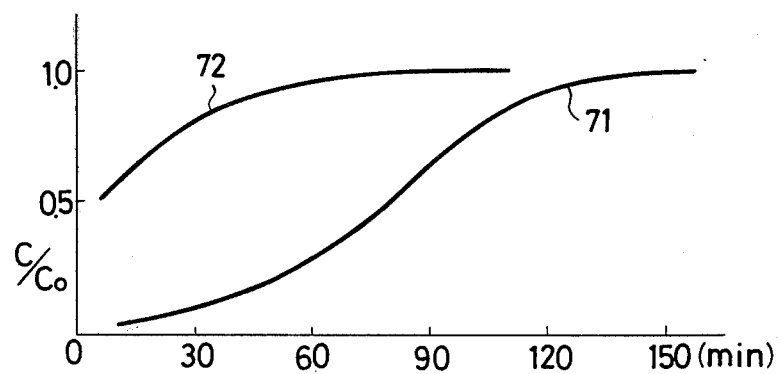
FIG. 7 is a graph showing a comparative example of deodorization capacity between a sanitary napkin of the present invention and a conventional napkin.

The deodorizing effect was tested between the sanitary napkin in the Example 1 and the normal sanitary napkin having the same structure without containing active carbon, to obtain the results shown in the following table and FIG. 7.

In this test, 210 ppm concentration isovaleric acid, which is known as one of typical uncomfortable odors, and whose odor limit concentration is 0.00062 ppm, was used as an odor gas, and two kinds of napkins cut in 4 cm diameter were used as bodies to be tested, and the odor gas was passed through each napkin under the same condition. But, the waterproofing layer (shown as numeral 54 in FIG. 5) that was positioned in the inside of each napkin enclosure was removed so as to promote passage of the odor gas. In the odor gas, the flow velocity was 0.066 cm/sec., the flow volume was 50 cc/min., the temperature was 30°C, and the humidity was 0 at the test time. In FIG. 7, Co represents a gas concentration before passing through each tested body, C represents a gas concentration after passing through each tested body, and C/Co represents a value for testing the deodorizing capacity of each tested body. 71 and 72 are curves of the tested bodies formed by plotting the values for testing the odor capacity against time, the former numeral represents the curve for the napkin in the Example 1, and the latter represents the curve for the normal napkin. The absorbed amounts in the following table are calculated from the integrated area of the partial curves to $C/Co = 1.0$, namely extending till the absorption capacity becomes zero. The values in the A and A' columns in the table represent absorbed gas amounts in the napkins and the values in B and B' columns are values that the absorbed gas amounts of the normal napkins are reduced from the values in A and A' columns, representing gas amounts absorbed by the active carbon purely contained in the napkins in the Example 1.

It is to be understood from the following table, the absorbed gas amount in the napkin in the Example 1 was about 6.2 times ($24.3/3.9 = 6.2$) of that of the normal napkin. Also, though the normal napkin became zero in the deodorizing capacity after about 60 min. from the time when isovaleric acid gas was passed through, the napkin in the Example 1 needed about 150 min. to reach the same condition.

TABLE

| Items | | Tested Result | |
|---|---|---|---|
| | | Normal Sanitary Napkin | Sanitary Napkin in Example 1 |
| Absorbed amount per tested body in 4 cm diameter (mg/4 cm diameter tested body | $A_1$ | 0.44 | 2.72 |
| | $B_1$ | 0 | 2.28 |
| Absorbed amount per one sanitary napkin (mg/piece) | A | 3.9 | 24.3 |
| | B | 0 | 20.4 |
| Ratio of absorbed amounts | 1 | 6.2 | |

Example 2

The structure of the sanitary napkin to be tested was made by dispersing and mixing about 4% by weight of 120 mesh active carbon powder into the absorbent layer 53a of the napkin for the cottony pulp in the layer instead of the sheet containing active carbon in the sanitary napkin in Example 1, and forming the other parts similarly to Example 1. The deodorizing effect was tested for the sanitary napkin in Example 2 and the normal sanitary napkin having the same structure without containing active carbon by the same method as Example 1. Consequently, it was found that the deodorizing effect of the sanitary napkin in Example 2 was almost similar to that of the sanitary napkin in Example 1, and the absorbed gas amount was about 6.4 times of that of the normal sanitary napkin.

Example 3

Figure 3:
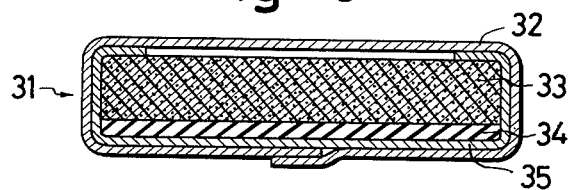
FIG. 3 is a sectional view taken along the X—X line in the FIG. 1 showing another embodiment.

The structure of the sanitary napkin to be tested was formed similarly to the structure in FIG. 3 described in the foregoing, where the same materials corresponding to the cover member and water-proofing layers in the sanitary napkin in Example 1 were used for the cover member 32, water-proofing layers 34 and 35, and the absorbent layer 33 was prepared by mixing the same amounts of 120 mesh silica and active carbon into N-BSP powder. Then the mixed deodorizer was about 3% by weight for one sanitary napkin of 6 g. The deodorizing effect was tested for the sanitary napkin in Example 3 and the normal sanitary napkin having the same structure without containing the deodorizer to find that the deodorizing effect of the sanitary napkin in Example 1, and the absorbed gas amount was about 5.9 times of that of the normal sanitary napkin.

Example 4

Figure 2:
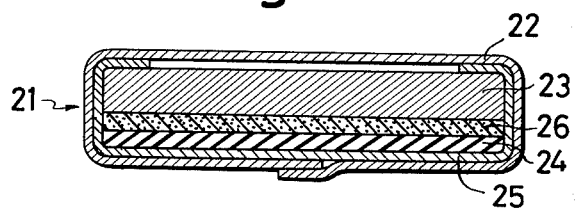
FIG. 2 is a sectional view taken along the X—X line in FIG. 1 showing one embodiment.

The structure of the sanitary napkin to be tested was formed similarly to that in the FIG. 2 described in the foregoing, where the same materials corresponding to the cover member and water-proofing members in the sanitary napkin in Example 1 were used for the cover member 22, water-proofing layers 24 and 25, and two sheets prepared by containing 40% of about 150 mesh active alumina and active carbon powder in N-BKP sheets of 25 g/m$^2$ scaled amount were used as the deodorizing sheet 26. Then the mixed deodorizer was 3.3% by weight for one sanitary napkin of 6 g. Deodorizing effect was tested for the sanitary napkin in Example 4 and the normal sanitary napkin having the same structure without containing the deodorizer by the same method as Example 1, to find that the deodorizing effect of the sanitary napkin in Example 4 was almost similar to that in Example 1, and the absorbed gas amount was about 5.6 times of that of the normal sanitary napkin.

Example 5

The structure of the sanitary napkin to be tested was formed similarly to that in the FIG. 2 described in the foregoing, where the same materials corresponding to the cover member and water-proofing layers in the sanitary napkin in Example 1 were used for the cover member 22, the water-proofing layers 24 and 25, and three sheets prepared by spraying a chlorophyl solution of 30% concentration in ethyl alcohol toward N-BKP sheets of 25 g/m$^2$ scaled amount to attach 30% by weight of chlorophyl for the pulp sheets were used as the deodorizing sheet 26. Then the chlorophyl crystal was 3.75% by weight for one 6 g sanitary napkin. The deodorizing effect was tested for the sanitary napkin in the Example 5 and the normal sanitary napkin having the same structure without containing the deodorizer by the same method as Example 1, to find that the deodorizing effect of the sanitary napkin in Example 5 was almost similar to that in Example 1.

The invention has been described in detail with particular reference to the preferred embodiments thereof, but it will be understood that variations and modifications can be effected within the spirit and scope of the invention.

What is claimed is:

1. An article for treating menstrual fluid comprising: a cover member forming an enclosure, said cover member being made of a porous non-woven sheet of cellulose fiber and artificial fiber; a cottony thin web attached to the inside of said enclosure; an absorbent layer means positioned within said enclosure and said web for absorbing the menstrual fluid; a first water-proofing layer means positioned under said absorbent layer means; a deodorizer means located within said enclosure and having the function of absorbing and holding the menstrual fluid and simultaneously removing the odor released from the menstrual fluid; and a second water-proofing layer means in contact with the cottony web and positioned under and around the sides of said first water-proofing layer, said absorbent layer and said deodorizer means; said first and second water-proofing layers defining means for preventing any menstrual fluid not absorbed by the absorbent layer from permeating to the outside of said cover member.

2. An article for treating menstrual fluid as defined in claim 1 wherein said deodorizer means consists of at least one material selected from the group consisting of active carbon, active silica, active alumina and ion exchange resin.

* * * * *